US010646360B2

(12) United States Patent
Stengel

(10) Patent No.: US 10,646,360 B2
(45) Date of Patent: May 12, 2020

(54) VESSEL IMPLANT FOR THE TREATMENT OF AN ANEURYSM

(71) Applicant: Max Stengel, Bruchsal (DE)

(72) Inventor: Max Stengel, Bruchsal (DE)

( * ) Notice: Subject to any disclaimer, the term of this patent is extended or adjusted under 35 U.S.C. 154(b) by 0 days.

(21) Appl. No.: 13/953,094

(22) Filed: Jul. 29, 2013

(65) Prior Publication Data

US 2013/0310922 A1 Nov. 21, 2013

Related U.S. Application Data

(62) Division of application No. 12/105,665, filed on Apr. 18, 2008, now abandoned.

(30) Foreign Application Priority Data

Apr. 23, 2007 (DE) ......................... 10 2007 019 058

(51) Int. Cl.
    *A61F 2/82* (2013.01)
    *A61F 2/07* (2013.01)
    (Continued)

(52) U.S. Cl.
    CPC .................. *A61F 2/82* (2013.01); *A61F 2/07* (2013.01); *A61F 2/848* (2013.01); *A61F 2/90* (2013.01);
    (Continued)

(58) Field of Classification Search
    CPC ........ A61F 2250/0039; A61F 2002/077; A61F 2/07; A61F 2/06; A61F 2/848;
    (Continued)

(56) References Cited

U.S. PATENT DOCUMENTS 5,609,627 A   3/1997  Goicoechea et al.
5,653,743 A * 8/1997  Martin ...................... A61F 2/07
                                                         606/153

(Continued)

FOREIGN PATENT DOCUMENTS

EP   1698302   6/2006
EP   1985258   10/2009

OTHER PUBLICATIONS

European Patent Office, Search Report issued in European Patent Application No. 08007336.4, dated Oct. 15, 2009, 8 pages.

*Primary Examiner* — Seema Mathew
(74) *Attorney, Agent, or Firm* — Glass and Associates; Kenneth D'Alessandro; Kenneth Glass

(57) ABSTRACT

A vessel implant for the treatment of an aneurysm, i.e. a dilatation of the cross-sectional area of a blood vessel, may include an elongate body having an inlet opening, an outlet opening, and a passage connecting the inlet opening to the outlet opening for the blood flowing through the blood vessel. The passage may be bounded in the peripheral direction by a blood-impermeable wall and the inlet opening may have a larger cross-sectional area than the outlet opening. The body may be provided with blood-permeable fixing means for the end of the body at the outlet opening side. The fixing means may be designed for contact with the vessel wall of the blood vessel. The fixing means may be designed to hold the body spaced apart from the vessel wall of the blood vessel in the region of the outlet opening.

12 Claims, 5 Drawing Sheets

(51) Int. Cl.
- *A61F 2/848* (2013.01)
- *A61F 2/06* (2013.01)
- *A61F 2/90* (2013.01)

(52) U.S. Cl.
CPC ... *A61F 2002/065* (2013.01); *A61F 2230/005* (2013.01); *A61F 2250/0039* (2013.01); *A61F 2250/0069* (2013.01)

(58) Field of Classification Search
CPC ...... A61F 2002/8483; A61F 2002/8486; A61F 2002/30327; A61F 2/95; A61F 2/82; A61F 2/852; A61F 2002/823
USPC ........................................................ 623/1.35
See application file for complete search history.

(56) References Cited

U.S. PATENT DOCUMENTS

| | | | | |
|---|---|---|---|---|
| 5,683,450 | A * | 11/1997 | Goicoechea et al. | 606/194 |
| 5,855,597 | A * | 1/1999 | Jayaraman | A61F 2/2412 623/1.16 |
| 5,876,445 | A * | 3/1999 | Andersen | A61F 2/04 623/23.7 |
| 5,922,019 | A * | 7/1999 | Hankh | A61F 2/90 606/198 |
| 6,102,938 | A * | 8/2000 | Evans | A61F 2/07 623/1.35 |
| 6,106,548 | A | 8/2000 | Roubin et al. | |
| 6,120,534 | A * | 9/2000 | Ruiz | A61B 17/12109 606/194 |
| 6,273,900 | B1 * | 8/2001 | Nott | A61F 2/01 606/159 |
| 6,458,153 | B1 * | 10/2002 | Bailey | A61F 2/2418 623/1.24 |
| 8,048,140 | B2 * | 11/2011 | Purdy | A61F 2/07 623/1.13 |
| 8,834,551 | B2 * | 9/2014 | McGuckin, Jr. | A61F 2/2418 623/1.11 |
| 2002/0173836 | A1 * | 11/2002 | Pinchuk | A61F 2/07 623/1.12 |
| 2002/0198587 | A1 * | 12/2002 | Greenberg | A61F 2/07 623/1.13 |
| 2003/0130611 | A1 * | 7/2003 | Martin | A61F 2/07 604/8 |
| 2003/0149472 | A1 | 8/2003 | Pinchuk et al. | |
| 2003/0236567 | A1 | 12/2003 | Elliot et al. | |
| 2004/0049258 | A1 | 3/2004 | Khosravi et al. | |
| 2004/0098099 | A1 * | 5/2004 | McCullagh | A61F 2/90 623/1.15 |
| 2004/0220653 | A1 * | 11/2004 | Borg | A61F 2/954 623/1.11 |
| 2004/0236411 | A1 * | 11/2004 | Sarac | A61F 2/2415 623/1.26 |
| 2004/0249439 | A1 * | 12/2004 | Richter | A61F 2/90 623/1.15 |
| 2005/0070992 | A1 * | 3/2005 | Bolduc | A61B 17/064 623/1.15 |
| 2005/0085894 | A1 * | 4/2005 | Kershner | A61F 2/07 623/1.13 |
| 2005/0102018 | A1 * | 5/2005 | Carpenter | A61F 2/07 623/1.11 |
| 2006/0064156 | A1 * | 3/2006 | Thistle | A61F 2/90 623/1.16 |
| 2006/0122685 | A1 * | 6/2006 | Bonsignore | A61F 2/07 623/1.13 |
| 2006/0149360 | A1 * | 7/2006 | Schwammenthal | A61F 2/2418 623/1.24 |
| 2006/0184238 | A1 * | 8/2006 | Kaufmann | A61F 2/90 623/1.53 |
| 2006/0195172 | A1 * | 8/2006 | Luo | A61F 2/07 623/1.13 |
| 2006/0287704 | A1 | 12/2006 | Hartley et al. | |
| 2007/0021828 | A1 * | 1/2007 | Krolik | A61F 2/91 623/1.31 |
| 2007/0088425 | A1 * | 4/2007 | Schaeffer | A61F 2/07 623/1.13 |
| 2007/0213813 | A1 * | 9/2007 | Von Segesser | A61F 2/2418 623/2.18 |
| 2007/0244520 | A1 * | 10/2007 | Ferren | A61B 1/00156 607/2 |
| 2007/0255389 | A1 * | 11/2007 | Oberti | A61F 2/90 623/1.11 |
| 2008/0140189 | A1 * | 6/2008 | Nguyen | A61F 2/2412 623/2.11 |
| 2008/0255678 | A1 * | 10/2008 | Cully | A61F 2/04 623/23.65 |
| 2009/0062901 | A1 * | 3/2009 | McGuckin, Jr. | A61F 2/2418 623/1.15 |
| 2009/0125098 | A1 * | 5/2009 | Chuter | A61F 2/07 623/1.26 |
| 2009/0270971 | A1 * | 10/2009 | Xiao | A61F 2/07 623/1.14 |
| 2009/0276040 | A1 * | 11/2009 | Rowe | A61B 17/0401 623/2.18 |
| 2010/0217382 | A1 * | 8/2010 | Chau | A61F 2/2418 623/1.26 |
| 2011/0029059 | A1 * | 2/2011 | Christiansen | A61F 2/07 623/1.2 |
| 2011/0093060 | A1 * | 4/2011 | Cartledge | A61B 17/07207 623/1.15 |
| 2011/0118821 | A1 * | 5/2011 | Brocker | A61F 2/07 623/1.16 |
| 2012/0022639 | A1 * | 1/2012 | Hacohen | A61F 2/2439 623/2.11 |
| 2012/0035647 | A1 * | 2/2012 | Bregulla | A61F 2/01 606/200 |
| 2012/0150274 | A1 * | 6/2012 | Shalev | A61F 2/856 623/1.12 |
| 2013/0282103 | A1 * | 10/2013 | Madjarov | A61F 2/06 623/1.15 |
| 2014/0364944 | A1 * | 12/2014 | Lutter | A61F 2/2487 623/2.17 |
| 2018/0021155 | A1 * | 1/2018 | Hadley | A61F 2/0031 623/1.15 |

* cited by examiner

VESSEL IMPLANT FOR THE TREATMENT OF AN ANEURYSM

CROSS-REFERENCE TO RELATED APPLICATIONS

This application is a divisional of U.S. patent application Ser. No. 12/105,665, filed Apr. 18, 2008, which claims priority to German Patent Application No. 10 2007 019 058.3, filed Apr. 23, 2007, both of which are hereby incorporated by reference as if set forth herein.

BACKGROUND

The present disclosure relates to a vessel implant for the treatment of an aneurysm, comprising an elongate body which has an inlet opening, an outlet opening as well as a passage connecting the inlet opening with the outlet opening for blood flowing through the blood vessel, with the passage being bounded in the peripheral direction by a blood-impermeable wall.

An aneurysm is a pathological, spatially restricted dilatation, swelling or expansion of a flood vessel, in particular of an artery. Aneurysms can occur at any section of an artery. Abdominal aortic aneurysms or aneurysms at the popliteal artery occur particularly frequently. Dilated blood vessels are subject to a high risk of rupture so that there is a risk of fatal bleeding. Furthermore, dilated blood vessels tend to become larger. The risk of rupture increases as the diameter of the aneurysm increases since the pressure exerted on the vessel wall of the blood vessel by the blood flowing through the blood vessel increases as the vessel width increases (Bernoulli's Law).

It is known to treat such dilated blood vessels using tubular or hose-shaped implants which are also called stents. In this connection, a stent having a blood-impermeable wall is inserted into the affected blood vessel such that the aneurysm can be bridged by means of the stent. In this connection, the two ends of the stent are fixed in as shape matched a manner as possible at the non-dilated regions of the blood vessel adjoining the dilated region at both sides, whereby a seal of the dilatation should be achieved to prevent blood from continuing to flow into the dilatation. The diameter of such a stent approximately corresponds to the normal diameter of a vessel.

There is, however, the problem with these solutions that small leaks can frequently occur, due to insufficient adaptation to the vessel, between the stent and that region of the vessel wall of the blood vessel at which the stent is fixed. Blood can continue to flow into the aneurysm, in particular due to leaks present at the inlet opening side or due to collateral vessels so that the risk of rupture of the vessel wall in the region of the aneurysm is not eliminated.

It is therefore the underlying object of the disclosure to provide a vessel implant of the initially named kind which reduces the risk of a rupture of the vessel wall in the region of an aneurysm.

This object is satisfied by a vessel implant having the features of claim 1 and in particular in that the inlet opening has a larger cross-sectional area than the outlet opening.

SUMMARY

The vessel implant is preferably fixed at its end having the inlet opening and/or at a section directly adjoining the inlet opening to the non-dilated region of the blood vessel disposed upstream of the aneurysm. The vessel implant preferably has a length which can extend over the total length of the aneurysm.

In accordance with the continuity law for non-compressible fluids, the same blood volume exits the outlet opening of the body that has flown into the body at the inlet opening of the body, i.e. the volume flow or the volume moving through a cross-section of the body within a unit of time is the same at the inlet opening and at the outlet opening. It results from this that the blood flowing through the blood vessel and thus through the body passes through the outlet opening at a higher speed than through the inlet opening. An underpressure by which the blood located in an aneurysm is sucked out arises at the end of the body having the outlet opening—as with a water jet pump—due to the higher speed. In this way, a corresponding underpressure also arises inside the aneurysm so that the dilated vessel wall is relieved.

This effect even occurs when the vessel implant is not completely sealed at the inlet opening side. The risk of a rupture of the vessel wall of the aneurysm can thus be effectively reduced using the vessel implant made in accordance with the present disclosure.

Because a seal of the aneurysm at the downstream side by the vessel implant is not required and does not even have to be 100% upstream of the seal, the vessel implant can also be used in those cases in which a sealing fixing at the blood vessel is not possible upstream and/or downstream of the aneurysm. Since a seal is not necessary downstream of the aneurysm, the vessel implant in accordance with the present disclosure can also be used with an abdominal aortic aneurysm which starts directly at the branch to the two femoral arteries. A fixation downstream of the aneurysm can either be dispensed with or a blood-permeable fixation can be used. For an abdominal aortic aneurysm starting directly at the branches to the two renal arteries, the vessel implant can be provided with a fixation section which in particular adjoins the inlet opening of the body directly and which is made blood-permeable in order not to close the branches to the renal arteries.

In accordance with an exemplary embodiment of the presently claimed invention, the body, a section of the body located between the inlet opening and the outlet opening and/or the passage from the inlet opening to the outlet opening converges and/or converge. A gradual reduction of the cross-sectional area from the inlet opening to the outlet opening can hereby be achieved over the total length of the body to avoid turbulence in the blood flow, for example. The convergence is preferably made uniformly, continuously and/or conically.

The body is preferably made for contact at the vessel wall of the blood vessel in the region of the inlet opening and/or at a section of the body adjoining the inlet opening. The outer cross-sectional area of the body is in particular dimensioned in the region of the inlet opening and/or of the section adjoining the inlet opening such that the body contacts the vessel wall of the blood vessel in the region of the inlet opening and/or at the section adjoining the inlet opening in the implanted state. A fixation of the body in the blood vessel can hereby be achieved.

To achieve a particularly good fixation of the vessel implant in the blood vessel, it can be advantageous for the section of the body adjoining the inlet opening to be cylindrical. The body can thus be adapted to the internal diameter of the blood vessel over a larger region.

It is particularly preferred for the section of the body adjoining the inlet opening to have a wall made permeable to blood. The section adjoining the inlet opening can be made as a mesh, for example. An ingrowth of the cells of the vessel wall of the blood vessel into the body of the implant is hereby promoted and thus a particularly firm fixation achieved.

In accordance with a further exemplary embodiment of the presently claimed invention, the outer dimension of the body is dimensioned in the region of the outlet opening such that the body is spaced apart from the vessel wall of the blood vessel in the region of the outlet opening. This can in particular be the case when the outer dimension of the body also converges toward the side having the outlet opening in addition to the cross-sectional area of the passage.

The body is preferably provided with blood-permeable fixation means for the end of the body at the outlet opening side, said means being made for contact with the vessel wall of the blood vessel. A lateral migration of the end of the body having the outlet opening to and fro in the blood flow can hereby be prevented so that a radial fixation is achieved within the blood vessel. The fixing means are made blood-permeable to impede a sucking of the blood out of the aneurysm effected by the generated underpressure as little as possible.

The fixing means can be made to keep the body spaced apart from the vessel wall of the blood vessel in the region of the outlet opening. It is hereby ensured that the end of the body having the outlet opening does not contact the vessel wall of the blood vessel so that the previously explained water jet pump effect can occur over the full peripheral area around the outlet opening. The fixing means can in particular be made such that the outlet opening or the end of the body having the outlet opening is held in centered form inside the blood vessel.

In accordance with a further exemplary embodiment of the presently claimed invention, the fixing means are provided in the region of the outlet opening at the body.

The fixing means can be made as a mesh, as a plurality of fixing elements respectively projecting from the body with a radial component and/or as a conical stent.

The body or a part thereof can be made in one piece with the fixing means. The fixing means can, however, also be made as a separate part or as separate parts which is/are connected to the body or to a part thereof.

The wall of the body can be rigid, flexible or partly rigid and flexible. The wall can, for example, be a mesh in the form of a stent which is provided with a coating. The coating can be provided at the outside, at the inside or both at the outside and at the inside of the mesh. The wall is preferably made of biocompatible material. The mesh can, for example, be made as a self-expanding stent or as a balloon-expanding stent. Whereas the vessel implant in a rigid embodiment is inserted into the blood vessel surgically, for example, a transluminal implantation is possible with an embodiment which is at least partly flexible.

The vessel implant, in particular the body or the wall of the body, can have a multi-part structure. In this case, the individual parts can be introduced into the blood vessel and/or deposited within the blood vessel separately from one another. With a multi-part wall, for example, which includes a blood-impermeable envelope and a support structure for the envelope, for example a mesh, the envelope can be introduced into the blood vessel and/or deposited within the blood vessel separately from the support structure and/or separately from fixing means for the body. On a separate introduction, for example disposed in series on a catheter or sequentially in each case with different catheters, the access for the catheter can be selected to be smaller so that the wound healing is improved.

It is, for example, possible that first only the envelope is introduced and deposited, with said envelope preferably being held at an end by the introduction instrument after the deposition. The support structure can subsequently be inserted into the envelope so that on the expansion of the support structure, the envelope is also expanded at the same time and is pressed through the support structure toward the vessel wall and is held there. If desired, the fixing means can be introduced in a next step and can be connected to the body formed by the support structure and the envelope.

The wall can also only include a blood-impermeable envelope, in particular without a support structure. The envelope can then, for example, be fastened to a section of the body adjoining the inlet opening upstream, in particular separate from the envelope, or can be pressed by it against the vessel wall for fastening. In this case, the support structure preferably has a short length so that it only comes to lie upstream of the aneurysm or only projects into the aneurysm over an in particular very short part region.

The present invention further relates to a vessel implant, comprising two bodies which are each made as explained above, with the bodies being connected to one another in the region of their inlet openings at a branch of the vessel implant. Such a vessel implant can, for example, be used with an abdominal aortic aneurysm in the region of the branch to the two femoral arteries.

The two bodies can in particular have a common section adjoining the branch for the contact with the vessel wall of the blood vessel.

BRIEF DESCRIPTION OF THE DRAWINGS

Non-restricting embodiments of the invention are shown in the drawings and will be described in the following. The drawings are shown, schematically in each case.

DETAILED DESCRIPTION

Figure 1:
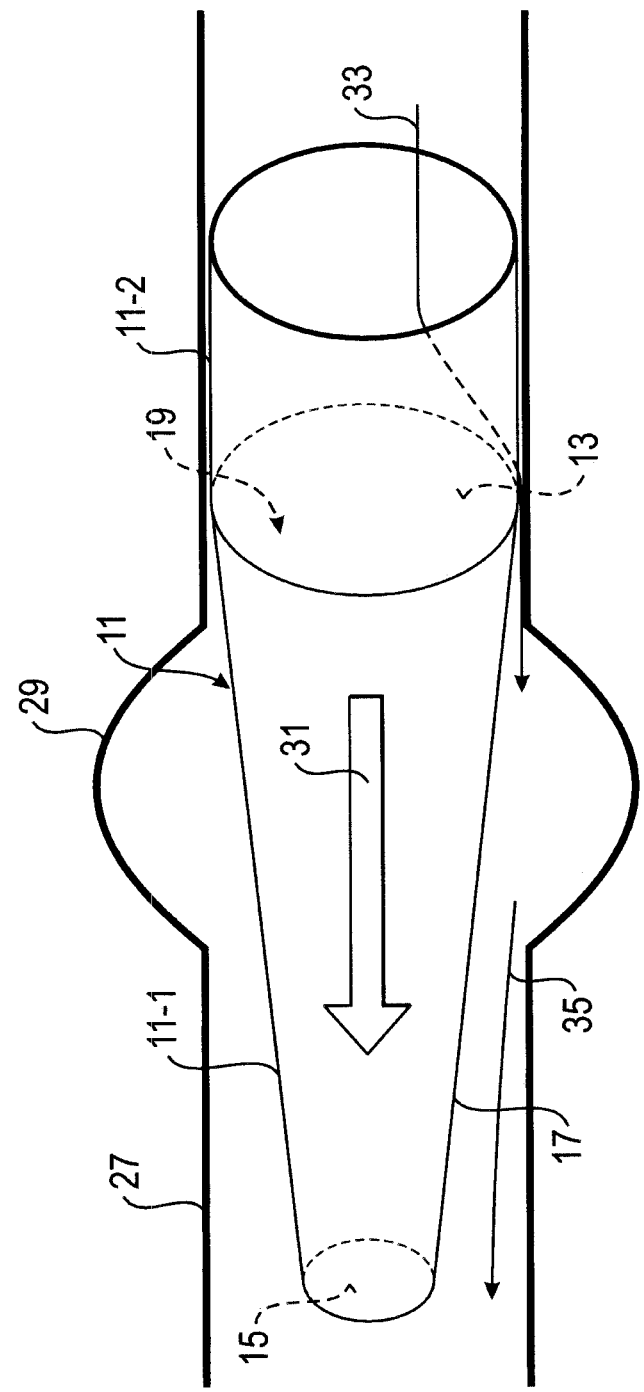
FIG. 1 shows a first embodiment of a vessel implant.

The vessel implant shown in FIG. 1 includes an elongate tubular body 11 which is divided into a section 11-1 and a section 11-2. The section 11-1 of the body 11 is conical and has a blood-impermeable wall 17. In the longitudinal direction, the section 11-1 is bounded by an inlet opening 13 and an outlet opening 15 which are connected to one another by a conical passage 19 which is bounded by the wall 17 in the radial direction. The second section 11-2 is cylindrical and directly adjoins the first section 11-1 of the body 11 at the inlet opening side. The second section 11-2 is, however, optional and can also be omitted.

The inlet opening 13 has a larger cross-sectional area than the outlet opening 15, i.e. the inner diameter or the lumen of the inlet opening 13 is larger than the inner diameter or lumen of the outlet opening 15.

The vessel implant with the body 11 is inserted into a blood vessel 27 which has a cross-sectional area dilatation 29, i.e. an aneurysm, locally. The body 11 contacts the vessel wall of the blood vessel 27 with its cylindrical section 11-2 and in the region of the inlet opening 13 in a region of the blood vessel not dilated, with the outer diameter of the cylindrical section 11-2 and the outer diameter in the region of the inlet opening 13 being selected to be slightly larger than the inner diameter of the blood vessel 27 such that the cylindrical section 11-2 of the body 11 contacts the vessel wall under tension, whereby a firm holding of the vessel implant is achieved. The section 11-2 is made as a mesh to promote an ingrowth of the cells of the vessel wall of the blood vessel 27.

The fixing of the cylindrical section 11-2 can take place in a manner known per se. The body 11 of the vessel implant can, for example, be made as a self-expanding stent, in particular consisting of nitinol, which is introduced into the blood vessel 27 by means of a catheter in a compressed state and automatically expands into a state with a larger radius after deposition due to the blood temperature so that the cylindrical section 11-2 contacts the vessel wall. It is also possible that the body 11 of the vessel implant is made, for example, of stainless steel or of spring steel and is in particular expanded via a balloon until the cylindrical section 11-2 comes into contact with the vessel wall.

The body 11 opens freely in the blood vessel 27 at the outlet opening side. The length of the body 11 is sufficient to completely span the aneurysm 29. It is, however, also generally also conceivable for the outlet opening 15 of the body 11 to be located in the region of the aneurysm 29 as long as it is ensured that an underpressure is generated inside the aneurysm 29 due to the described water jet pump effect.

Blood flowing through the blood vessel 27 in the direction of flow 31 enters via the cylindrical section 11-2 and through the inlet opening 13 into the conical section 11-1 of the body 11 and leaves it through the outlet opening 15, with the flow rate increasing constantly within the conical section 11-2 due to the continuously narrowing passage 19.

Blood which passes between the vessel wall of the blood vessel 27 and the conical section 11-1 of the body 11 comprising the blood-impermeable wall 17 in the region of the inlet opening 13 through a leak in accordance with an arrow 33 and which collects in the aneurysm 29 is conveyed in the direction of flow 31 due to the water jet pump effect described above by the blood flowing out of the outlet opening 15 at an increased rate so that an underpressure arises inside the aneurysm 29 and the build-up of too high a pressure onto the vessel wall of the blood vessel 27 in the region of the aneurysm 29 can be prevented. The pressure difference occurring due to the underpressure between the aneurysm 29 and the region of the blood vessel 27 surrounding the outlet opening 15 of the body 11 is illustrated by an arrow 35.

Figure 2:
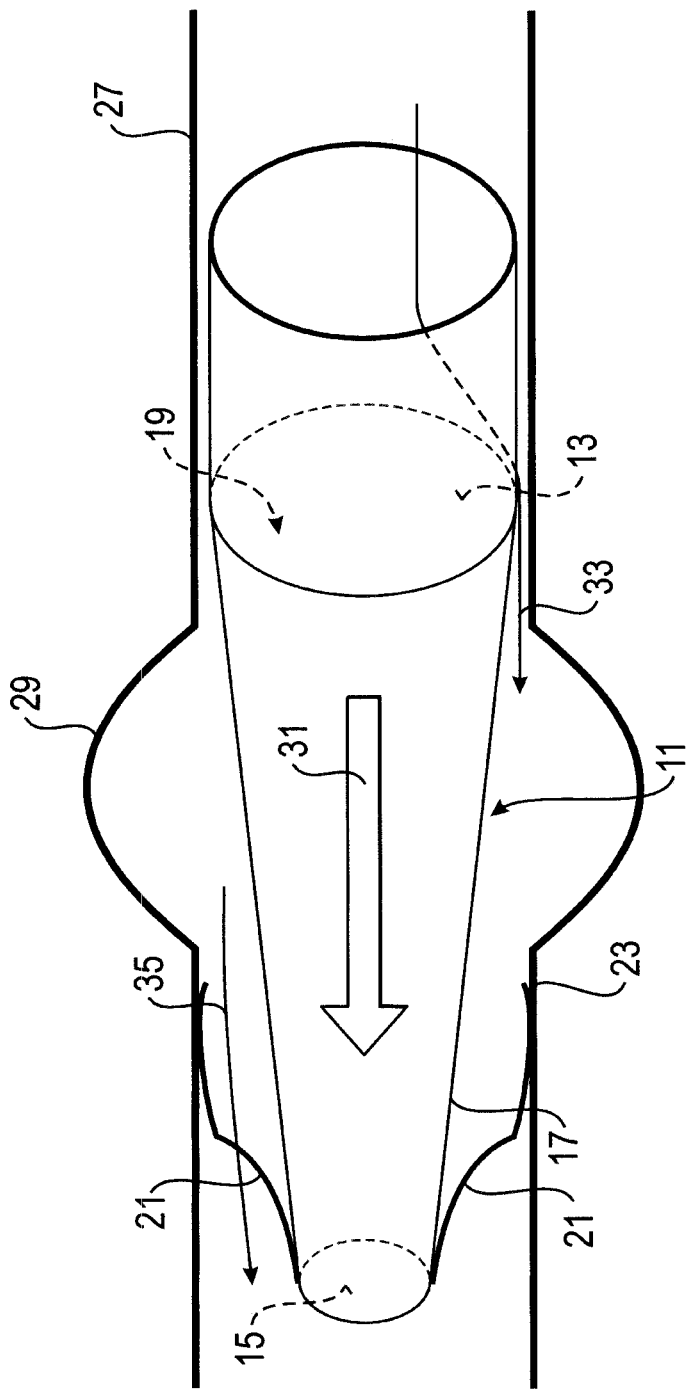
FIG. 2 shows the vessel implant from FIG. 1 with fixing elements in accordance with the presently claimed invention.

The vessel implant shown in FIG. 2 substantially corresponds to the vessel implant shown in FIG. 1. In contrast to FIG. 1, the vessel implant in accordance with FIG. 2, however, has a conical stent 21 with a blood-permeable wall which converges in the same direction as the conical section 11-1 of the body 11. The conical stent 21 having a larger opening angle than the conical body section 11-1 is attached at its tapered end to the body 11 in the region of the outlet opening 15. The conical stent 21 is made as a fixing means and is supported at its end points 23 remote from the body 11 at the vessel wall of the blood vessel 27. The body 11 is hereby held spaced apart from the vessel wall of the blood vessel 27 in the region of the outlet opening 15 and in a centered fashion within the blood vessel 27.

Figure 3:
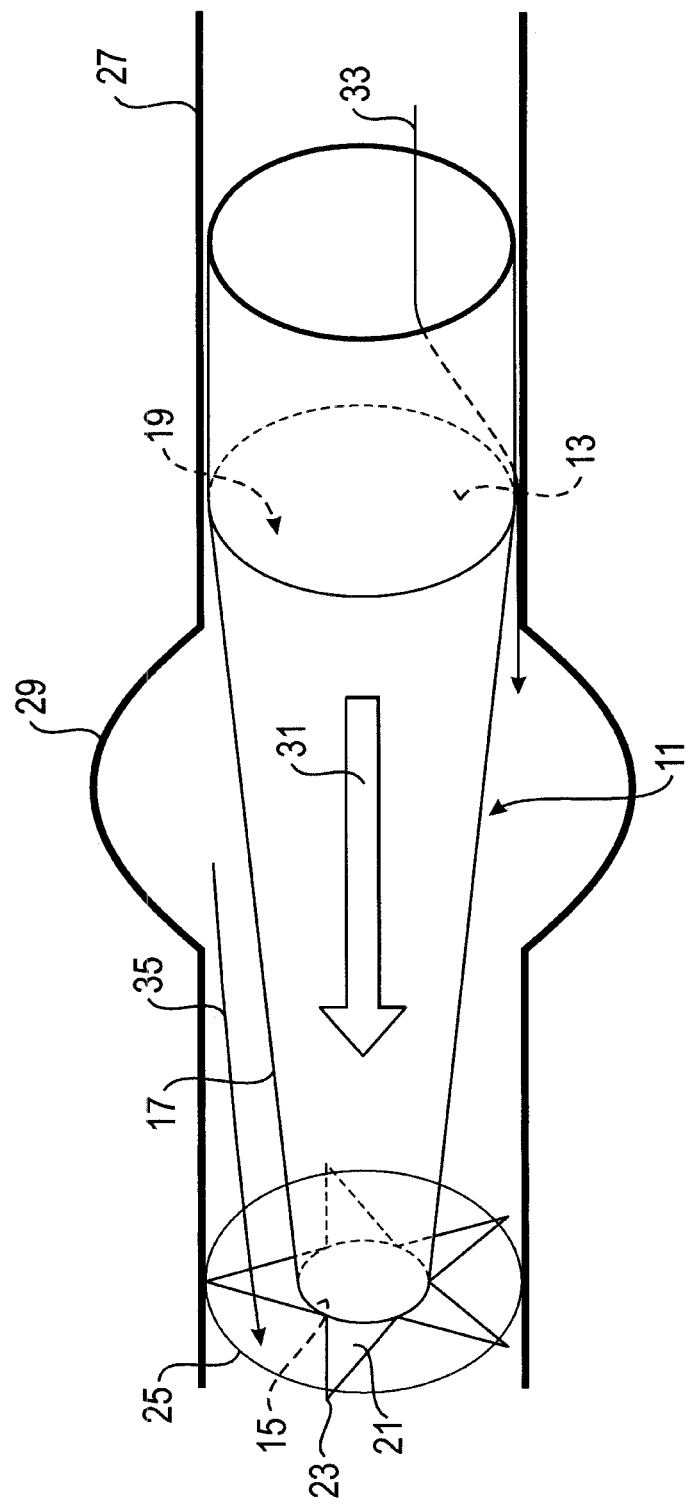
FIG. 3 shows the vessel implant from FIG. 1 with star-shaped fixing means in accordance with the presently claimed invention.
Figure 4:
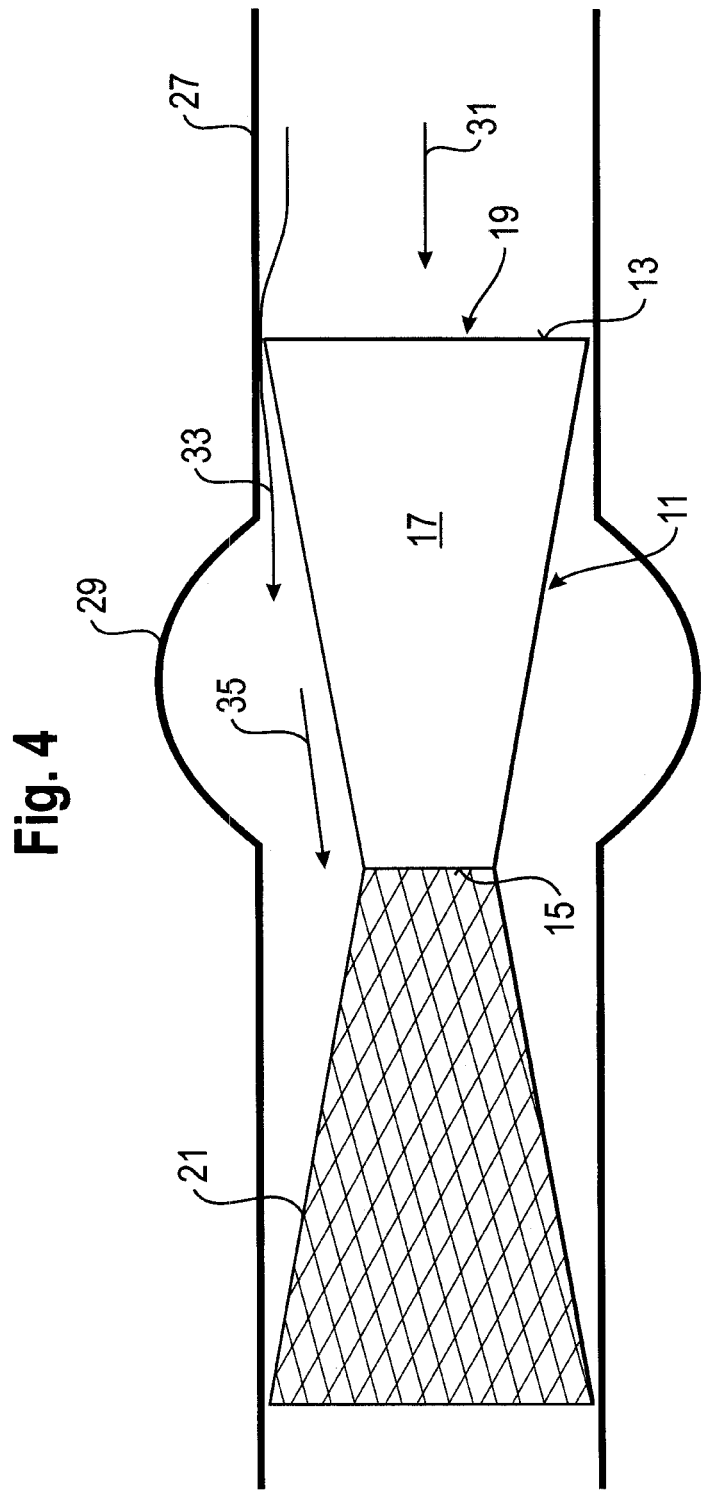
FIG. 4 shows the vessel implant from FIG. 1 with fixing means in accordance with the presently claimed invention made as a conical stent.

The fixing means 21 shown in FIG. 2 are, however, only of an exemplary nature. Blood-permeable fixing means of any desired other form can generally be provided which can hold the end of the body 11 comprising the outlet opening 15 spaced apart from the vessel wall of the blood vessel 27 and centered within the blood vessel 27. A plurality of radially outwardly projecting fixing elements 21 can in particular be provided. In FIG. 3, the fixing elements 21 are made, for example, in the form of a star whose end points 23 remote from the body 11 are arranged on an imaginary circular line 25 which is dimensioned such that the end points 23 contact the vessel wall of the blood vessel 27. In the vessel implant shown in FIG. 4, the fixing means are made as a blood-permeable conical stent 21 which consists of a mesh so that overall a double truncated cone-shaped vessel implant is formed which has a restriction centrally. The fixing means 21 shown in FIGS. 2 to 4 can each be made in one piece with the body 11 or can be connected to the body 11 in the region of the outlet opening 15.

Figure 5:
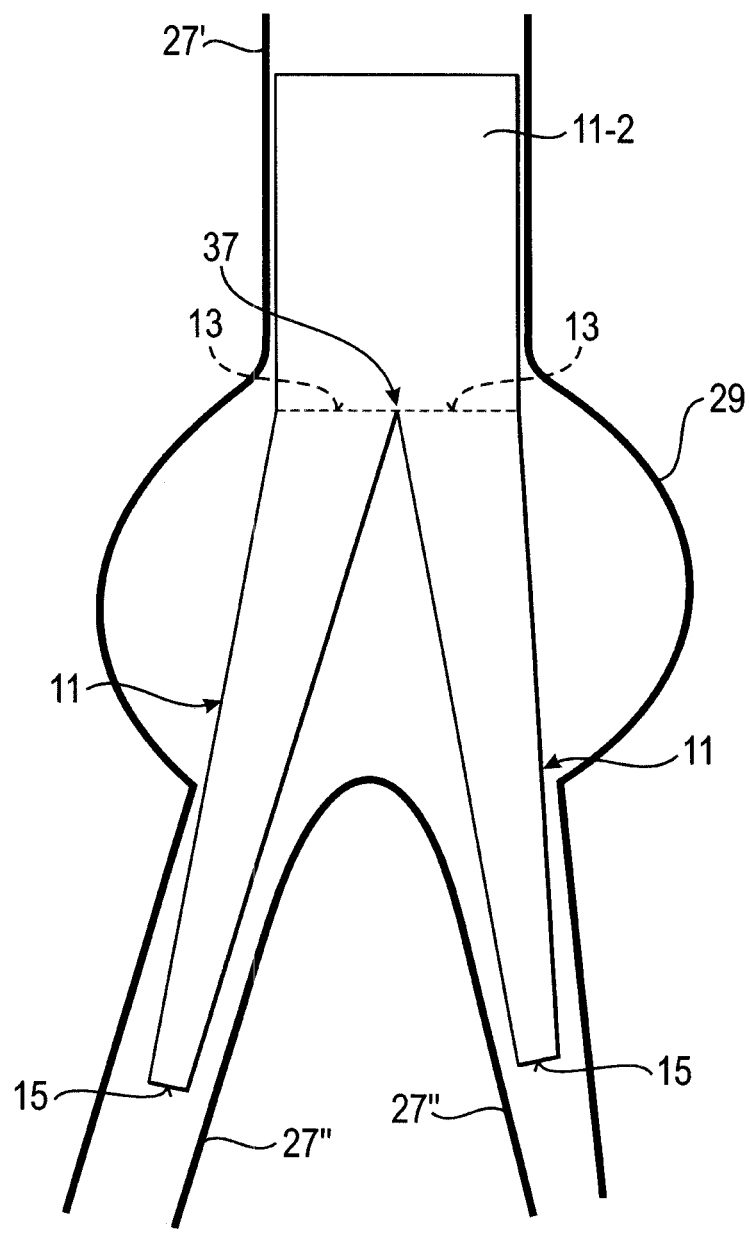
FIG. 5 shows a further embodiment of a vessel implant.

The vessel implant shown in FIG. 5 is made at least substantially Y-shaped and includes two bodies 11 which are essentially as described above and which are each conical. The two bodies 11 are connected to one another in the region of their respective entry openings 13 at a branch 37 of the vessel implant, with a common cylindrical section 11-2 being provided for the two bodies 11. The vessel implant in accordance with this embodiment is in particular suitable to be used with an abdominal aortic aneurysm 27, with the cylindrical section 11-2 being fixed upstream of the aneurysm 29 in the abdominal aorta 27' in the implanted state and being largely sealed with respect to the vessel wall at least in the transition region to the inlet openings 13 and with the outlet openings 15 of the two bodies 11 each ending in a fixed or unfixed state in a respective femoral artery 27".

The following description of preferred embodiments of the invention is not intended to limit the scope of the invention to these preferred embodiments, but rather to enable any person skilled in the art to make and use the invention.

As any person skilled in the art will recognize from the previous description and from the figures and claims, modifications and changes can be made to the preferred embodiments of the invention without departing from the scope of the invention defined in the following claims.

What is claimed is:

1. A vessel implant for the treatment of an aneurysm, comprising an elongate body having an inlet opening, an outlet opening, and a passage tapering from the inlet opening to the outlet opening, the passage connecting the inlet opening to the outlet opening in a direction of the unidirectional flow of blood through the blood vessel for the blood flowing through the blood vessel, the passage being bounded in the peripheral direction by a blood-impermeable wall, characterized in that the inlet opening has a larger cross-sectional area than the outlet opening and is larger than the outlet opening, wherein the body is provided with blood-permeable fixing means for the end of the body at the outlet opening side, said fixing means being designed for contact with the vessel wall of the blood vessel, said fixing means being designed to hold the body spaced apart from the vessel wall of the blood vessel in the region of the outlet opening, and said fixing means having a radial component projecting outwardly from the body.

2. A vessel implant in accordance with claim 1, characterized in that the body, a section of the body located between the inlet opening and the outlet opening and/or the passage converges/converge from the inlet opening toward the outlet opening.

3. A vessel implant in accordance with claim 2, characterized in that the convergence is uniform, continuous and/or conical.

4. A vessel implant in accordance with claim 1, characterized in that the body is designed for contact with the vessel wall of the blood vessel in the region of the inlet opening and/or at a section of the body adjoining the inlet opening.

5. A vessel implant in accordance with claim 4, characterized in that the section of the body adjoining the inlet opening is cylindrical.

6. A vessel implant in accordance with claim 4, characterized in that the section of the body adjoining the inlet opening has a blood permeable wall.

7. A vessel implant in accordance with claim 1, characterized in that the outer dimension of the body is dimensioned in the region of the outlet opening such that the body is spaced apart from the vessel wall of the blood vessel in the region of the outlet opening.

8. A vessel implant in accordance with claim 1, characterized in that the fixing means are provided at the body in the region of the outlet opening.

9. A vessel implant in accordance with claim 1, characterized in that the body or a part thereof is made in one piece with the fixing means.

10. A vessel implant in accordance with claim 1, characterized in that the wall of the body is rigid, flexible or partly rigid and partly flexible.

11. A vessel implant in accordance with claim 1, characterized in that the vessel implant, in particular the body or the wall of the body, is made in multiple parts.

12. A vessel implant for the treatment of an aneurysm, comprising:
an elongate body having an inlet opening, an outlet opening, and a passage connecting the inlet opening to the outlet opening for the unidirectional flow of blood through the blood vessel from the inlet opening to the outlet opening, the passage being bounded in the peripheral direction by a blood-impermeable wall, characterized in that the inlet opening has a larger cross-sectional area than the outlet opening and is larger than the outlet opening, and the passage tapers from the inlet opening to the outlet opening; and
a blood-permeable fixing section disposed at the end of the body at the outlet opening side sized for contact with the vessel wall of the blood vessel and having a radial component projecting outwardly from the body in more than one polar direction to hold the body spaced apart from the vessel wall of the blood vessel in the region of the outlet opening.

* * * * *